United States Patent
Zuk

(10) Patent No.: US 10,451,616 B2
(45) Date of Patent: *Oct. 22, 2019

(54) WIDE RANGE LUMINESCENT IMMUNOASSAYS

(71) Applicant: Access Medical Systems, LTD., Palo Alto, CA (US)

(72) Inventor: Robert F. Zuk, Menlo Park, CA (US)

(73) Assignee: Access Medical Systems, LTD., Palo Alto, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 15/429,362

(22) Filed: Feb. 10, 2017

(65) Prior Publication Data

US 2017/0153231 A1 Jun. 1, 2017

Related U.S. Application Data

(63) Continuation of application No. 13/794,080, filed on Mar. 11, 2013, now Pat. No. 9,568,431.

(Continued)

(51) Int. Cl.
*G01N 33/543* (2006.01)
*G01N 21/76* (2006.01)
(Continued)

(52) U.S. Cl.
CPC ....... *G01N 33/54306* (2013.01); *G01N 21/66* (2013.01); *G01N 21/76* (2013.01);
(Continued)

(58) Field of Classification Search
CPC .. G01N 21/66; G01N 33/54306; G01N 21/76; G01N 33/582; G01N 2458/30; G01N 2458/40; G01N 33/5308
See application file for complete search history.

(56) References Cited

U.S. PATENT DOCUMENTS

| 3,996,345 A | 12/1976 | Ullman et al. |
| 4,200,613 A | 4/1980 | Alfrey et al. |

(Continued)

FOREIGN PATENT DOCUMENTS

| CN | 1784603 A | 6/2006 |
| CN | 102341696 A | 2/2012 |

(Continued)

OTHER PUBLICATIONS

International Search Report and Written Opinion of PCT Application No. PCT/US2013/036389 dated Jul. 12, 2013.

(Continued)

*Primary Examiner* — Richard A Schnizer
*Assistant Examiner* — Gary E Hollinden
(74) *Attorney, Agent, or Firm* — Perkins Coie LLP; Viola T. Kung

(57) ABSTRACT

The present invention relates to a method for quantitating an analyte having a wide range concentration in a single assay without having to dilute the sample and repeating the assay. The key feature of the invention is having two cycles of events including sample binding to probe, binding reactions, and detection. After the first cycle of binding and detecting, the probe is dipped into the same sample vessel to bind additional analyte in the sample vessel at a condition that is more favorable to binding than the condition in the first cycle.

12 Claims, 7 Drawing Sheets

Related U.S. Application Data

(60) Provisional application No. 61/624,924, filed on Apr. 16, 2012.

(51) Int. Cl.
  *G01N 21/66* (2006.01)
  *G01N 33/58* (2006.01)
  *G01N 33/53* (2006.01)

(52) U.S. Cl.
  CPC ....... *G01N 33/5308* (2013.01); *G01N 33/582* (2013.01); *G01N 2458/30* (2013.01); *G01N 2458/40* (2013.01)

(56) References Cited

U.S. PATENT DOCUMENTS

| | | | |
|---|---|---|---|
| 4,208,479 A | 6/1980 | Zuk et al. |
| 4,272,510 A | 6/1981 | Smith et al. |
| 4,276,259 A | 6/1981 | Eibl et al. |
| 4,434,150 A | 2/1984 | Azad et al. |
| 4,447,546 A | 5/1984 | Hirschfeld |
| 4,483,925 A | 11/1984 | Noack |
| 4,599,315 A | 7/1986 | Terasaki et al. |
| 4,778,751 A | 10/1988 | El Shami et al. |
| 4,822,565 A | 4/1989 | Kohler |
| 4,891,321 A | 1/1990 | Hubscher |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,320,814 A | 6/1994 | Walt et al. |
| 5,449,625 A | 9/1995 | Kobayashi et al. |
| 5,486,616 A | 1/1996 | Waggoner et al. |
| 5,494,830 A | 2/1996 | Hubscher |
| 5,650,334 A | 7/1997 | Zuk et al. |
| 5,814,524 A | 9/1998 | Walt et al. |
| 6,146,593 A | 11/2000 | Pinkel et al. |
| 6,197,597 B1 | 3/2001 | Tuunanen |
| 6,210,910 B1 | 4/2001 | Walt et al. |
| 6,667,159 B1 | 12/2003 | Walt et al. |
| 8,309,369 B2 | 11/2012 | Tan et al. |
| 8,647,889 B2 | 2/2014 | Zuk et al. |
| 2008/0182235 A1 | 7/2008 | Hearn et al. |
| 2010/0062544 A1 | 3/2010 | Evans et al. |
| 2011/0312105 A1 | 12/2011 | Tan et al. |
| 2013/0071952 A1 | 3/2013 | Zuk et al. |

FOREIGN PATENT DOCUMENTS

| | | |
|---|---|---|
| EP | 1879030 | 1/2009 |
| JP | 2004-205286 A | 7/2004 |
| JP | 2004-226307 A | 8/2004 |
| WO | WO 2005/064347 A1 | 7/2005 |
| WO | WO 2011-014946 | 2/2011 |
| WO | WO 2011/109379 A1 | 9/2011 |

OTHER PUBLICATIONS

Hagan et al.; "Lanthanide-Based Time-Resolved Luminescence Immunoassays"; Analytical & Bioanalytical Chemistry; vol. 400, No. 9, pp. 2847-2864 (May 11, 2011).

WIDE RANGE LUMINESCENT IMMUNOASSAYS

This application is a continuation of U.S. application Ser. No. 13/794,080, filed Mar. 11, 2013; which claims the benefit of U.S. Provisional Application No. 61/624,924, filed Apr. 16, 2012. The above identified applications are incorporated herein by reference in their entireties.

BACKGROUND OF THE INVENTION

In many situations in clinical diagnostics, certain samples quantified by immunoassays can generate out of high range values, i.e. the analyte concentration is higher than the level where the assay can produce accurate and reproducible results. There is a need to quantify these samples because patients producing such out of high range analyte samples often have a high incidence of morbidity and mortality demanding medical attention. Immunoassays are also useful tools in these clinical situations not only for diagnosis but as well to monitor therapy.

Standard laboratory practice with an out of high range sample is for the laboratory personnel to further dilute the sample so that the analyte concentration falls within the quantification range followed by a repeat second assay. This protocol is problematic in that the re-assay requires more time to result, which can be detrimental in acute care or emergency rooms, and further incurs additional reagent cost to the laboratory. Some common lateral flow immunoassay devices do not have a means to dilute samples, which compels the user to perform the subsequent assay on another instrument enabling sample dilution protocols.

Solid phase immunoassays have limitations with high range samples because analyte concentrations can exceed the binding capacity of the immobilized antibody. Some clinical assays further require the combination of ultra sensitive detection of low analyte levels and quantification of high amounts of analyte, consequentially a wide quantification range is desirable. B-type natriuretic peptide, NTproBNP, and procalcitonin are such examples.

Development of solid phase immunoassays with a wide quantification range with low and high level detection are opposed technical goals. For example, in order not to exceed the immobilized antibody binding capacity with high analyte levels, samples are highly diluted (1/10-1/100) or have short incubation times with the solid phase. Sensitive assays often require minimal sample dilutions (undiluted, ½-⅓) and relatively long incubation times with solid phase to effect binding of detectable amounts of trace analyte. The net result is often a compromise with less than adequate quantification range with either the low or high end of the analyte range having suboptimal clinical performance.

Arylsulfonate cyanine fluorescent dyes are described in Mujumdar et al. (1993) *Bioconjugate Chemistry*, 4:105-111; Southwick et al. (1990) *Cytometry*, 11:418-430; and U.S. Pat. No. 5,268,486. Cy5 is described in each of the references and is commercially available from Biological Detection Systems, Inc., Pittsburgh, Pa., under the tradename FLUOROLINK™ Cy5™. The arylsulfonate cyanine fluorescent dyes have high extinction coefficients (typically from 130,000 L/mole to 250,000 L/mole), good quantum yields, fluorescent emission spectra in a range (500 nm to 750 nm) outside of the autofluorescence wavelengths of most biological materials and plastics, good solubilities, and low non-specific binding characteristics.

Despite these excellent properties, arylsulfonate cyanine fluorescent dyes suffer from certain limitations. In particular, these dyes have a relatively narrow Stokes shift which results in significant overlap between the excitation and emission spectra of the dye. The overlap of excitation and emission spectra, in turn, can cause self-quenching of the fluorescence when the dye molecules are located close to each other when excited. Such self-quenching limits the number of arylsulfonate dye molecules which can be conjugated to a single antibody molecule for use in immunoassays. In the case of Cy5, an exemplary arylsulfonate cyanine fluorescent dye, the Stokes shift is 17 nm (which is the difference between an excitation wavelength of 650 nm and an emission wavelength of 667 nm). Optimal fluorescent yield is obtained when from two to four Cy5 molecules are conjugated to a single antibody molecule. The fluorescent signal output drops rapidly when more than four dye molecules are conjugated to a single antibody molecule. The inability to conjugate more than four dye molecules to individual antibody molecules significantly limits the sensitivity of immunoassays using Cy5-labelled antibodies and other binding substances.

U.S. Publication 2011/0312105 discloses a detection system and fluorescent immunoassays; the publication is incorporated herein by reference in its entirety.

There is a need for a method for quantitating an analyte having a wide range concentration in a single assay without having to dilute the sample and repeat the assay with fresh reagents.

DETAILED DESCRIPTION OF THE INVENTION

Definitions

Figure 1:
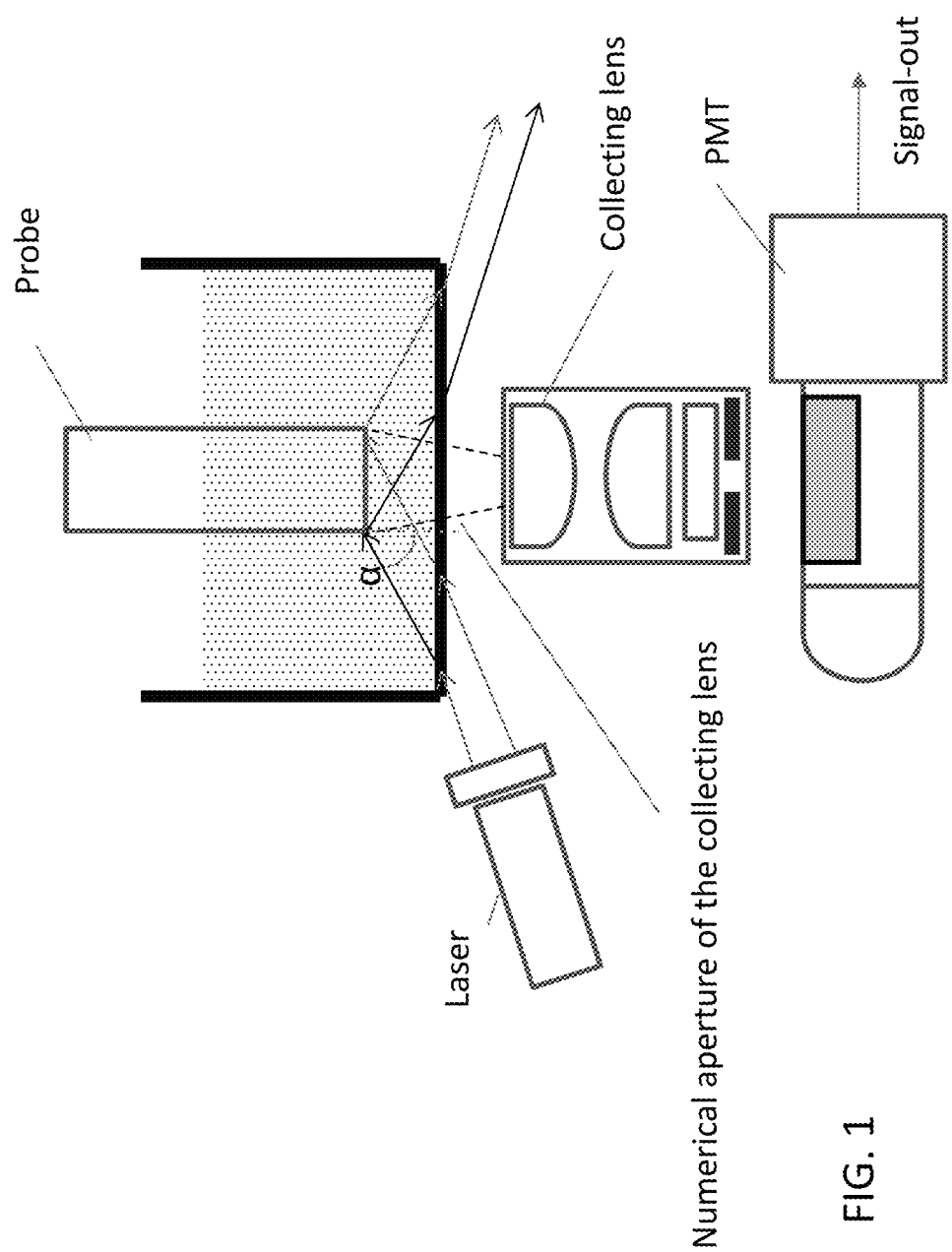
FIG. 1 illustrates an optical detecting system for detecting fluorescent signal from the sensing surface of the probe.

Terms used in the claims and specification are to be construed in accordance with their usual meaning as understood by one skilled in the art except and as defined as set forth below.

"About," as used herein, refers to within ±10% of the recited value.

An "analyte-binding molecule", as used herein, refers to any molecule capable of participating in a specific binding reaction with an analyte molecule.

An "aspect ratio" of a shape refers to the ratio of its longer dimension to its shorter dimension.

A "binding molecular," refers to a molecule that is capable to bind another molecule of interest.

A "binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, biotin and neutravidin (a deglycosylated version of avidin), lectin and carbohydrates. Preferred binding pairs are biotin and streptavidin, biotin and avidin, biotin and neutravidin, fluorescein and anti-fluorescein, digioxigenin/anti-digioxigenin, DNP (dinitrophenol)/anti-DNP.

A "branched polymer," as used herein, refers to a non-linear polymer having a 2- or 3-dimensional structure, which can be either a naturally occurring branched polymer, or a synthetically crosslinked polymer.

"Chemiluminescence," as used herein, refers to the emission of energy with limited emission of luminescence, as the result of a chemical reaction. For example, when luminol reacts with hydrogen peroxide in the presence of a suitable catalyst, it produces 3-aminophthalate in an excited state, which emits light when it decays to a lower energy level.

A "dendrimer," as used herein, refers to repetitively organic, branched molecules. A dendrimer is typically symmetric around the core, and often adopts a spherical three-dimensional morphology.

"Electrochemiluminescence," (ECL), as used herein, refers to luminescence produced during electrochemical reactions in solutions. In ECL, electrochemically generated intermediates undergo a highly exergonic reaction to produce an electronically excited state and then emits light. ECL excitation is caused by energetic electron transfer (redox) reactions of electrogenerated species. ECL is usually observed during application of potential (several volts) to electrodes of electrochemical cell that contains solution of luminescent species "Immobilized," as used herein, refers to reagents being fixed to a solid surface. When a reagent is immobilized to a solid surface, it is either be non-covalently bound or covalently bound to the surface.

A "monolithic substrate," as used herein, refers to a single piece of a solid material.

A "probe," as used herein, refers to a substrate coated with a thin-film layer of analyte-binding molecules at the sensing side. A probe has a distal end and a proximal end. The proximal end (also refers to probe tip in the application) has a sensing surface coated with a thin layer of analyte-binding molecules.

A "wide range concentration", as used herein, refers to a concentration range over at least 500-fold, 1000-fold, 2000-fold or 5000-fold.

The present invention is directed to a method for quantitating an analyte that has a wide range concentration in a single assay without having to dilute the sample and repeating the assay. The feature of the invention has two cycles of events each including sample binding to probe, binding reactions, and detection. In general, the assay conditions of the first cycle are optimized for samples at the high concentration end of the relevant clinical range, and the assay conditions of the second cycle are optimized for low concentration end of the relevant clinical range. After the first cycle of binding and detecting, the probe is re-dipped into the same sample vessel to bind additional analyte in the sample vessel to the probe in a more favorable binding condition (e.g., longer reaction time and/or agitation) than the binding condition in the first cycle. The analyte concentration is detected in both cycles, and the combined results provide the ability of quantitating an analyte that has a wide range concentration in a single assay without having to dilute the sample and re-do the assay. Another advantage of the present invention is that the wide range protocol uses the same sample and reagents in both cycles and does not require additional sample or reagents for the second cycle.

First Embodiment

In the first embodiment, the present method comprises the steps in the order of: (a) obtaining a probe having a first antibody immobilized on the tip of the probe, wherein the diameter of the tip surface is ≤5 mm; (b) dipping the probe tip into a sample vessel containing a sample solution having an analyte for 10 seconds to 2 minutes and flowing the sample solution laterally in the sample vessel at 0-500 rpm, preferably 0-200 rpm, to bind the analyte to the first antibody on the probe tip; (c) dipping the probe tip into a reagent vessel containing a reagent solution comprising a reagent of a second antibody conjugated with a first member of a binding pair to bind the reagent to the analyte; (d) dipping the probe tip into a first washing vessel containing a wash solution to wash the probe tip; (e) dipping the probe tip into an amplification vessel containing an amplification solution comprising a second member of the binding pair conjugated with one or more luminescent labels, to form an immunocomplex of the analyte, the first antibody, the second antibody, and the first and the second members of the binding pair on the probe tip; (f) dipping the probe tip into a second washing vessel containing a wash solution to wash the probe tip; (g) obtaining a first result by measuring the luminescent signal of the immunocomplex formed on the probe tip; (h) dipping the probe tip into the same sample vessel for 1-30 minutes and flowing the sample solution laterally in the sample vessel at 0-1200 rpm, preferably 200-1200 rpm or 200-1000 rpm, to bind additional analyte in the sample to the first antibody on the probe tip; (i) repeating steps (c) to (f) 1-10 times; (j) obtaining a second result by measuring luminescent signal of the final immunocomplex formed on the probe tip; and (k) combining the two results and analyzing the analyte concentration in a wide range; wherein the first antibody and the second antibody are antibodies against the analyte.

In step (a), the probe can be any shape such as rod, cylindrical, round, square, triangle, etc., with an aspect ratio of length to width of at least 5 to 1, preferably 10 to 1. A rod-shape is preferred. Because the probe is dipped in a sample solution and one or more assay solutions during an immunoassay, it is desirable to have a long probe with an aspect ratio of at least 5 to 1 to enable the probe tip's immersion into the solutions. For fluorescent assay, the probe can be a monolithic substrate.

The probe has a small tip for binding analytes. The tip has a smaller surface area with a diameter ≤5 mm, preferably ≤2 mm or ≤1 mm, e.g., 0.5-2 mm. The small surface of the probe tip provides several advantages. First, a small surface has less non-specific binding and thus produces a lower background signal. Second, the reagent or sample carry over on the probe tip is extremely small due to the small surface area of the tip. This feature makes the probe tip easy to wash, and causes negligible contamination in the wash solution since the wash solution has a larger volume. Further, small surface area of the probe tip has a small binding capacity. Consequently, when the probe tip is immersed in a reagent solution, the binding of the reagent does not consume a significant amount of the reagent. The reagent concentration is effectively unchanged. Negligible contamination of the wash solution and small consumption of the reagents enable the reagent solution, the amplification solution, and the wash solution to be re-used many times, for example, 1-10 times or 3-5 times.

The sensing surface of the probe is coated with first antibody which binds to the analyte in a sample. Methods to immobilize reagents to the solid phase (the sensing surface of the probe tip) are common in immunochemistry and involve formation of covalent, hydrophobic or electrostatic bonds between the solid phase and reagent. The first antibody can be directly immobilized on the sensing surface. Alternatively, the first antibody can be indirectly immobilized on the sensing surface through a binding pair. For example, anti-fluorescein can be first immobilized either by adsorption to the solid surface or by covalently binding to aminopropylsilane coated on the solid surface. Then the first antibody that is labeled with fluorescein can be bound to the solid surface through the binding of fluorescein and anti-fluorescein (binding pair).

In step (b), the probe tip is dipped into a sample vessel for 10 seconds to 2 minutes, preferably 30 seconds to 1 minute, to bind the analyte to the first antibody on the probe tip.

After step (b), the probe is optionally washed 1-5 times, preferably 1-3 times in a wash vessel containing a wash solution. This extra washing step may not be required because the amount of the carried-over solution is minimal due to a small binding surface area. The wash solution typically contains buffer and a surfactant such as Tween 20.

In step (c), the probe tip is dipped into a reagent vessel for 20 seconds to 10 minutes, preferably 20 seconds to 2 minutes to bind the reagent to the analyte on the probe tip. The reagent solution comprises a reagent of a second antibody conjugated with a first member of a binding pair.

The binding pair is typically a hapten and its antibody, a ligand and its receptor, complementary strands of nucleic acids, or lectin and carbohydrates. For example, the binding pair is biotin and streptavidin, biotin and avidin, biotin and neutravidin, fluorescein and anti-fluorescein, digioxigenin and anti-digioxigenin, and DNP (dinitrophenol) and anti-DNP. Preferably, the first member of the binding pair is biotin and the second member of the binding pair is streptavidin.

In Step (d), the probe is washed 1-5 times, preferably 1-3 times in a first wash vessel containing a wash solution. The wash solution typically contains buffer and a surfactant such as Tween 20.

In step (e), the probe is dipped into an amplification vessel containing an amplification solution for 20 seconds to 5 minutes, preferably 20 seconds to 2 minutes, to form an immunocomplex of the analyte, the first antibody, the second antibody, and the first and the second members of the binding pair on the probe tip. The amplification solution comprises a second member of the binding pair conjugated with one or more luminescent labels.

To improve the sensitivity of the assay, the amplification solution may comprise a polymer conjugated with at least 5 molecules of second member of the binding pair and at least 25 luminescent labels. The polymer is preferably branched and/or crosslinked. The polymer has a molecular weight of at least 500,000, preferably 1 million Daltons. The polymer can be a polysaccharide (e.g. FICOLL® (copolymers of sucrose and epichlorohydrin) or dextran), a polynucleotide, a dendrimer, a polyols, or polyethylene glycol. The polymer is preferably branched or crosslinked to have a 2- or 3-dimensional structure. The polymer preferably comprises 5-50 or 5-100 binding molecules and 25-100 or 25-500 luminescent molecules.

The luminescent label useful for this invention has a molecular weight of <5,000, preferably <2,000, such as 500-2000 or 100-2000 Daltons. In one embodiment, the luminescent label is a fluorescent dye selected from the group consisting of: cyanine, coumarin, xanthene and a derivative thereof. For example, the fluorescent dye is Cy5 (molecule weight MW 792), Alexa Fluor 647, DyLight 350 (MW 874), DyLight 405 (MW793), DyLight 488 (MW 71011), DyLight 550 (MW 982), DyLight 594 (MW 1078), DyLight 633 (MW 1066), DyLight 650 (MW 1008), DyLight 680 (MW 950), DyLight 755 (MW 1092), DyLight 800 (MW 1050), an Oyster fluorescent dye, IRDye, or organic compounds comprising multiple rings chelated with a rare earth metal such as a lanthanide (Eu, Th, Sm, or Dy).

In another embodiment, the luminescent label is a chemiluminescent marker selected from the group consisting of: Ruthenium(II)tris-bipyridine (MW 1057), luminol (MW 177), acridinium ester (9[[4-[3-[(2,5-dioxo-1-pyrrolidinyl) oxy]-3-oxopropyl]phenoxy]carbonyl]-10-methyl-acridinium trifluoromethane sulfonate, MW 632), hemin (MW 652).

When the binding molecule is a polypeptide or protein, the luminescent label can covalently bind to it through a variety of moieties, including disulfide, hydroxyphenyl, amino, carboxyl, indole, or other functional groups, using conventional conjugation chemistry as described in the scientific and patent literature.

Covalent binding of a binding molecule to a polynucleotide can be effected through a variety of moieties, including aldehyde, ketone, isothiocyanate, imidate, inosine, acyl, and alkyl, using conventional conjugation chemistry, while derivatization with biotin is taught in many references. (Leary et al. (1983) Proc. Natl. Acad. Sci. USA 80:4045-4049; WO86/02929; EP063 879; Langer et al. (1981) Proc. Natl. Acad. Sci. USA 78:6633-6637; and EP2009 996).

In each step (b), (c), and (e), the reaction can be accelerated by agitating or mixing the solution in the vessel. For example, a lateral flow (orbital flow) of the solution across the probe tip can be induced at 1-500 rpm, preferably 1-200 rpm, which accelerates the capture of target molecules by its binding partner immobilized to solid phase. For example, the reaction vessel can be mounted on an orbital shaker and the orbital shaker is rotated at a speed at least 50 rpm, preferably at least 200 rpm. Optionally, the probe tip can be moved up and down and perpendicular to the plane of the orbital flow, at a speed of 0.01 to 10 mm/second, in order to induce additional mixing of the solution above and below the probe tip.

In Step (f), the probe is washed 1-5 times, preferably 1-3 times in a second wash vessel containing a second wash solution. The wash solution typically contains buffer and a surfactant such as Tween 20. The first and the second wash vessels can be the same vessel or different vessels. The first and the second wash solutions can be the same or different solutions.

In Step (g), the immunocomplex is detected by reading the luminescent signal on the probe. For a fluorescent label, the probe is placed in a clear-bottom well and read by a detector, such as those described in US 2011/0312105 (FIG. 1), which is incorporated herein by reference.

For a chemiluminescent label, the probe is placed in a clear-bottom well containing a measurement solution having a co-reactant. For example, if the chemiluminescent label is Ruthenium(II)tris-bipyridine, the co-reactant is tripropylamine. If the chemiluminescent label is luminol, the co-reactants are hydrogen peroxide and a hydroxide salt in water. The light emitted is measured by a photomultiplier tube (PMT).

For electrochemiluminescence (ECL), the mechanism and the principal components of the ECL analyzer is described by Blackburn et al (Clin. Chem. 37: 1534-1539 (1991)), which is incorporated herein by reference. After the probe is placed in a clear-bottom well containing a measurement solution having a co-reactant, a voltage is applied to the working electrode and counter electrode, and the emitted light is measured by PMT.

Figure 2:
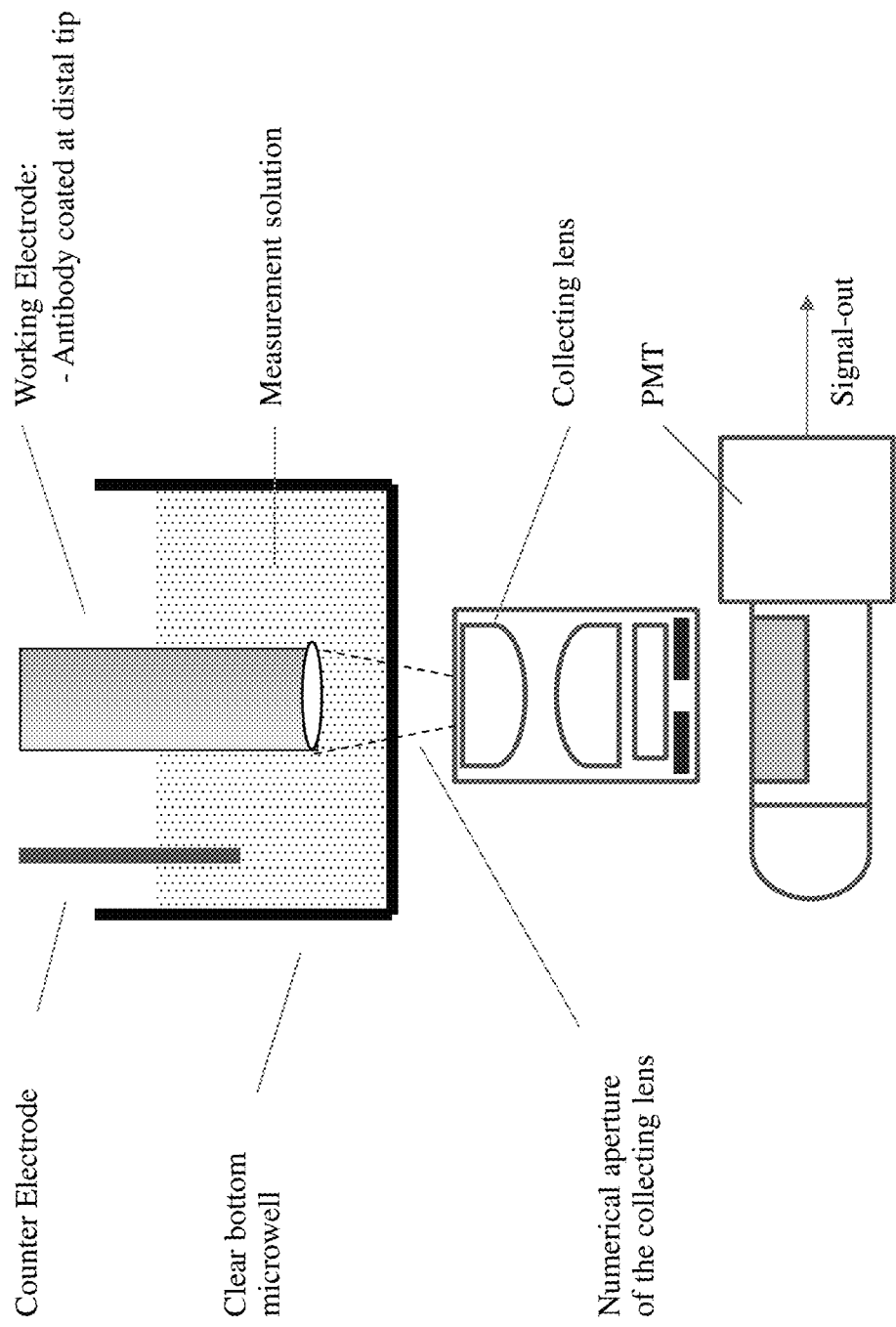
FIG. 2 illustrates an electrochemiluminescent detecting system for detecting chemiluminescent signal on the probe tip.

In a preferred embodiment, the antibody-coated probe serves as the working electrode of ECL analyzer (FIG. 2). This offers the advantage of efficient luminescence generation since the Ru(II)/tripropylamine red-ox reaction needs to occur at the electrode surface or very close proximity.

Step (h) starts the second cycle of events. Step (h) dips the probe tip back into the same sample vessels for a longer time of 1-30 minutes, preferably 2-30 minutes, or 3-30 minutes, and optionally agitates the same to increase the binding of additional analyte to the first antibody on the probe tip.

Step (i) is cycling amplification by repeating steps (c)-(f) 1-10 times, preferably 1-5 times, 1-3 times, or 2-3 times. When the amplification solution comprises a polymer conjugated with at least 5 molecules of second member of the binding pair and at least 25 luminescent labels, steps (c)-(f) can be repeated 2-10 times to increase assay signal and sensitivity. Each cycle consists of placing the probe back to the same reagent vessel, the same first wash vessel, the same amplification vessel, and the same second wash vessel. When the amplification solution does not comprise a high molecular weight polymer, steps (c)-(f) are typically repeated only one time.

Step (j) detects the final immunocomplex formed by measuring the luminescent signal on the probe tip and combining the two detection results to analyze the analyte concentration in a wide range and then combines the two detection results to analyze the analyte concentration in a wide range.

Figure 3:
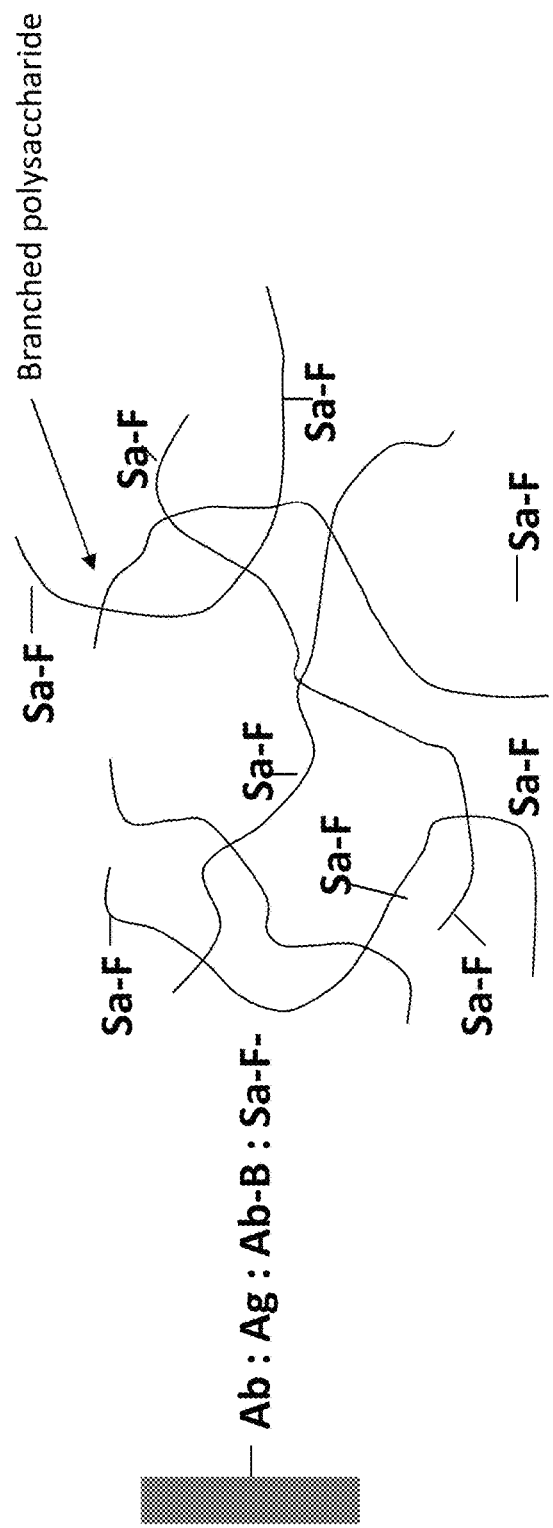
FIG. 3 illustrates an immunoassay format of the first embodiment of the invention for detecting an antigen analyte. Ab: antibody, Ag: antigen, Sa: streptavidin, B: biotin, F: fluorescent label.

FIG. 3 illustrates an immunoassay format of the first embodiment of the invention for detecting an antigen analyte.

Figure 4:
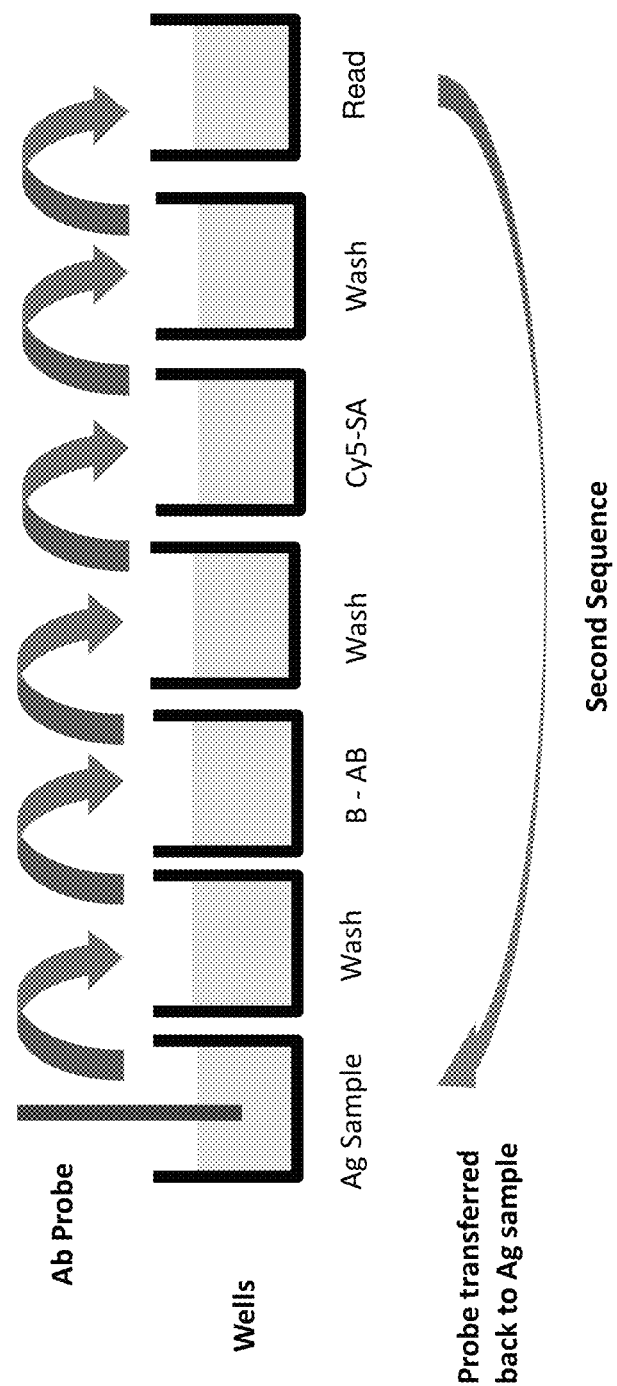
FIG. 4 illustrates a wide range protocol of the first embodiment of the invention.

FIG. 4 illustrates the probe transfer in wide range protocols of the first embodiment of the invention. In FIG. 4, the wide range protocol consists of two assay sequences with the same sample and reagents. The first sequence entails immersion of the antibody (Ab) coated probe in an antigen (Ag) sample vessel followed by immersion in a biotinylated-antibody (B-AB) reagent vessel and then immersion in a vessel comprising streptavidin conjugated with a fluorescent label (CyS-SA). Signal is read on the distal tip of the probe after the labeled streptavidin binding. For the second sequence, the probe is then transferred back to the same sample vessel where binding conditions are altered to effect greater binding and higher sensitivity. Typically, increasing the incubation time and/or increasing the orbital flow rate of the probe improves sensitivity of the sample binding. The probe is then transferred to the same biotinylated-antibody reagent vessel and then labeled streptavidin reagent vessel, followed by a second measurement.

Second Embodiment

In the second embodiment, the present method comprises the steps in the order of: (i) obtaining a probe having a first antibody immobilized on the tip of the probe, wherein the diameter of the tip surface is ≤5 mm; (ii) dipping the probe tip into a sample vessel containing a sample solution having an analyte for 10 seconds to 2 minutes and flowing the sample solution laterally in the sample vessel at 0-500 rpm, to bind the analyte to the first antibody on the probe tip; (iii) dipping the probe tip into a reagent vessel containing a reagent solution comprising a second antibody conjugated with fluorescent labels, to form an immunocomplex of the analyte, the first antibody, and the second antibody; (iv) dipping the probe tip into a washing vessel containing a wash solution to wash the probe tip; (v) obtaining a first result by measuring the luminescent signal of the first immunocomplex formed on the probe tip; (vi) dipping the probe tip into the same sample vessel for 1-30 minutes and flowing the sample solution laterally in the sample vessel at 0-1200 rpm, preferably 200-1200 rpm or 200-1000 rpm, to bind additional analyte in the sample to the first antibody on the probe tip; (vii) repeating steps (iii) and (iv); (viii) obtaining a second result by measuring the luminescent signal of the final immunocomplex formed on the probe tip; and (ix) combining the two results and analyzing the analyte concentration in a wide range; wherein the first antibody and the second antibody are antibodies against the analyte.

Steps (i) and (ii) of the second embodiment are similar to Steps (a) and (b) of the first embodiment.

In step (iii), the probe tip is dipped into a reagent vessel for 20 seconds to 10 minutes, preferably 20 seconds to 2 minutes to bind the reagent to the analyte on the probe tip. The reagent solution comprises a reagent of a second antibody conjugated with fluorescent labels. In one embodiment, the reagent solution comprises a polymer conjugated with at least 5 molecules of the second antibody and at least 25 luminescent labels, wherein the polymer has a molecular weight of at least 1 million Daltons, and the luminescent labels has a molecular weight of less than 2,000 Daltons. Suitable polymers are similar to those described in the first embodiment.

Steps (iv), (v), (vi), (viii) and (ix) are similar to steps (d), (g), (h), (j), and (k) of the first embodiment, respectively.

Figure 5:
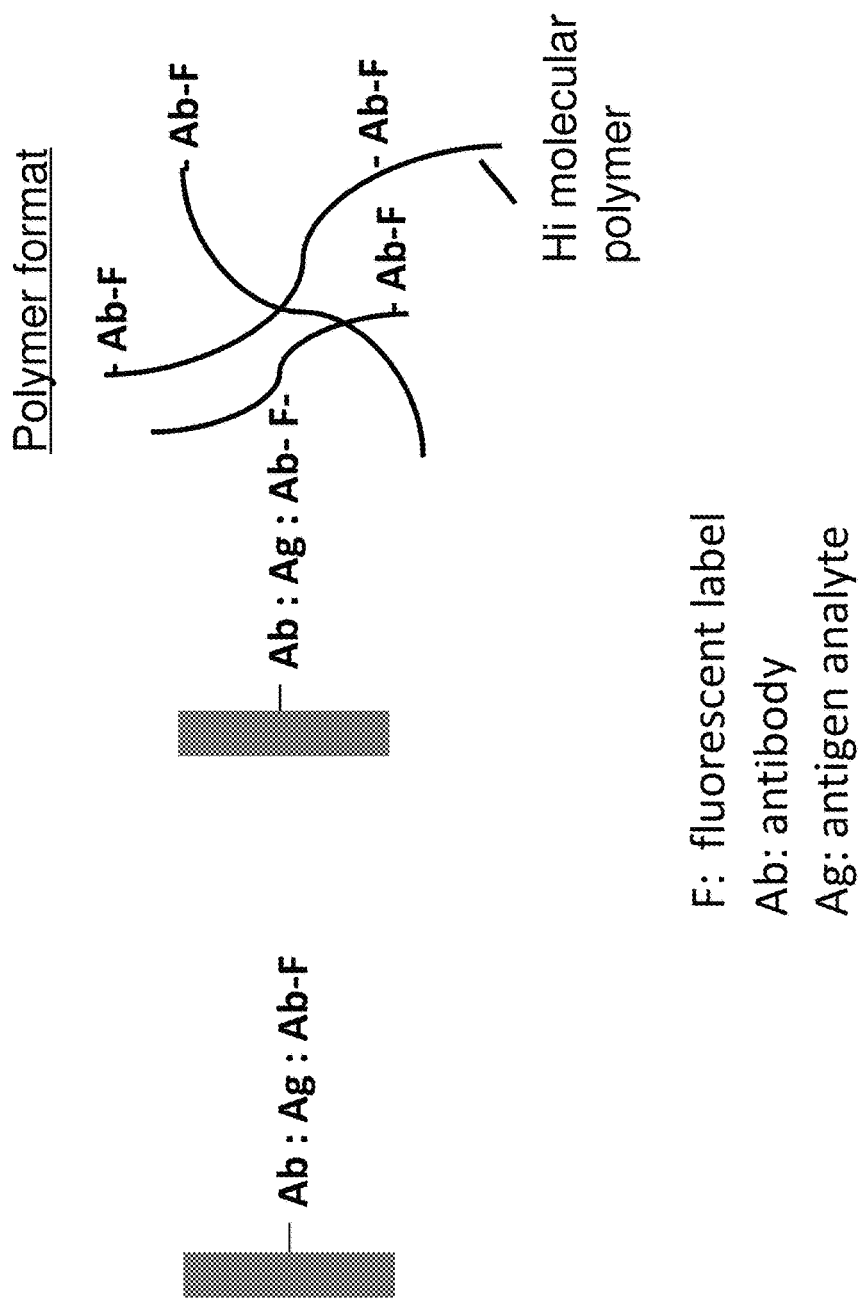
FIG. 5 illustrates an immunoassay format of the second embodiment of the invention for detecting an antigen analyte. Ab: antibody, Ag: antigen, F: fluorescent label.

FIG. 5 illustrates of an immunoassay format of the second embodiment of the invention for detecting an antigen analyte.

Figure 6:
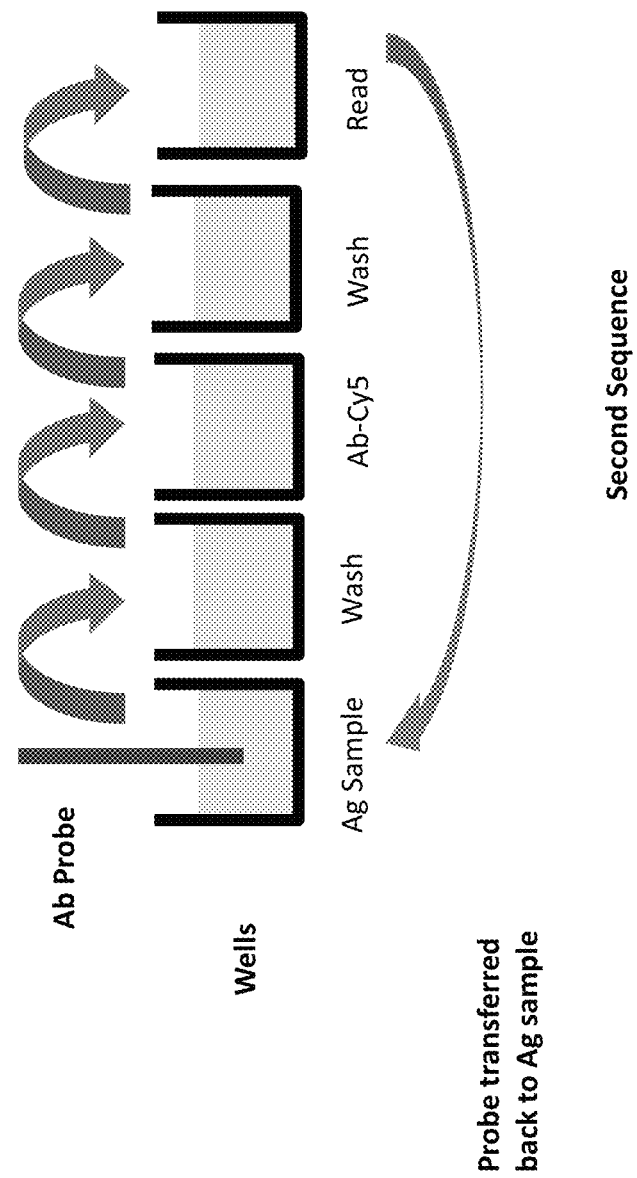
FIG. 6 illustrates a wide range protocol of the second embodiment of the invention.

FIG. 6 illustrates the probe transfer in wide range protocols of the second embodiment of the invention. In FIG. 6, the wide range protocol consists of two assay sequences with the same sample and reagents. The first sequence entails immersion of the antibody (Ab) coated probe in an antigen (Ag) sample vessel followed by immersion in a reagent vessel comprising an antibody conjugated with a fluorescent label (Ab-Cy5). Signal is read on the distal tip of the probe after the labeled antibody binding. For the second sequence, the probe is then transferred back to the same sample vessel where binding conditions are altered to effect greater binding and higher sensitivity. Typically, increasing the incubation time and/or increasing the orbital flow rate of the probe improves sensitivity of the sample binding. The probe is then transferred to the same reagent vessel, followed by a second measurement.

In general, the assay conditions of the first sequence are optimized for samples at the high concentration end of the relevant clinical range with low concentration samples being undetectable. The assay conditions of the second sequence are optimized for low concentration clinical samples with high concentration samples saturating the binding capacity of the probe. Cyclic amplification can be employed in either sequence, but rarely in the first sequence since high sensitivity is not required at that step.

The wide range protocol using a small surface area probe features two assay sequences using the same sample and reagents to extend an immunoassay's analytical range. The present invention has unexpected advantages over other heterogeneous immunoassay formats such as microwells, magnetic particles, or beads, which are commonly employed as the solid phase since they have relatively high surface areas to effect rapid capture of antigen. Their protocols entail adding, and after an incubation period, withdrawing sample and reagents from the solid phase. In between each reagent addition to the solid phase, a wash sequence is performed. The wash sequence also consists of adding then withdrawing the wash reagent from the solid phase. It adds to the complexity of performing the assay to have extra pipetting systems to enable re-use of sample and reagents. Secondly, the high surface area of the solid phase in other protocols may deplete the reagents or cause carry over in the wash cycles which could reduce assay performance.

The invention is illustrated further by the following examples that are not to be construed as limiting the invention in scope to the specific procedures described in them.

EXAMPLES

Example 1: Preparation of Probe Having Immobilized First Antibody

Basic natriuretic peptide (BNP) is a 32 amino acid polypeptide secreted by the ventricles of the heart in response to excessive stretching of heart muscle cells. The N-terminal prohormone of brain natriuretic peptide (NT-proBNP) is a 76 amino acid N-terminal fragment. Both BNP and NT-proBNP levels in the blood are used for screening, diagnosis of acute congestive heart failure and may be useful to establish prognosis in heart failure, Procalcitonin (PCT) is a peptide precursor of the hormone calcitonin, the latter being involved with calcium homeostasis. It is composed of 116 amino acids and is produced by parafollicular cells of the thyroid and by the neuroendocrine cells of the lung and the intestine.

Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of murine monoclonal anti-fluorescein (BiosPacific Inc.), 10 µg/ml in PBS (phosphate-buffered saline) at pH 7.4. After allowing the antibody to adsorb to the probe for 20 minutes, the probe tip was washed in PBS. Capture antibodies for BNP, NT-proBNP and PCT (HyTest, Finland) were labeled with fluorescein by standard methods. Typically, there were about 4 fluorescein substitutions per antibody. Anti-fluorescein coated probes were immersed in fluorescein labeled capture antibody solution, 5 µg/ml, for 5 minutes followed by washing in PBS.

Example 2: Preparation of Biotinylated Antibodies

Anti-BNP, anti-NT-proBNP and anti-PCT antibodies were labeled with biotins by standard methods. For example, biotinylated-NHS was reacted with the antibody at a molar ratio about 15 to 1 at room temperature in PBS (pH 7) for 1 hour. The biotinylated antibody was purified by Sephadex G-25 column. Typically, there were about 3-6 biotins per antibody.

Example 3. Preparation of Crosslinked FICOLL® 400-SPDP

Figure 7:
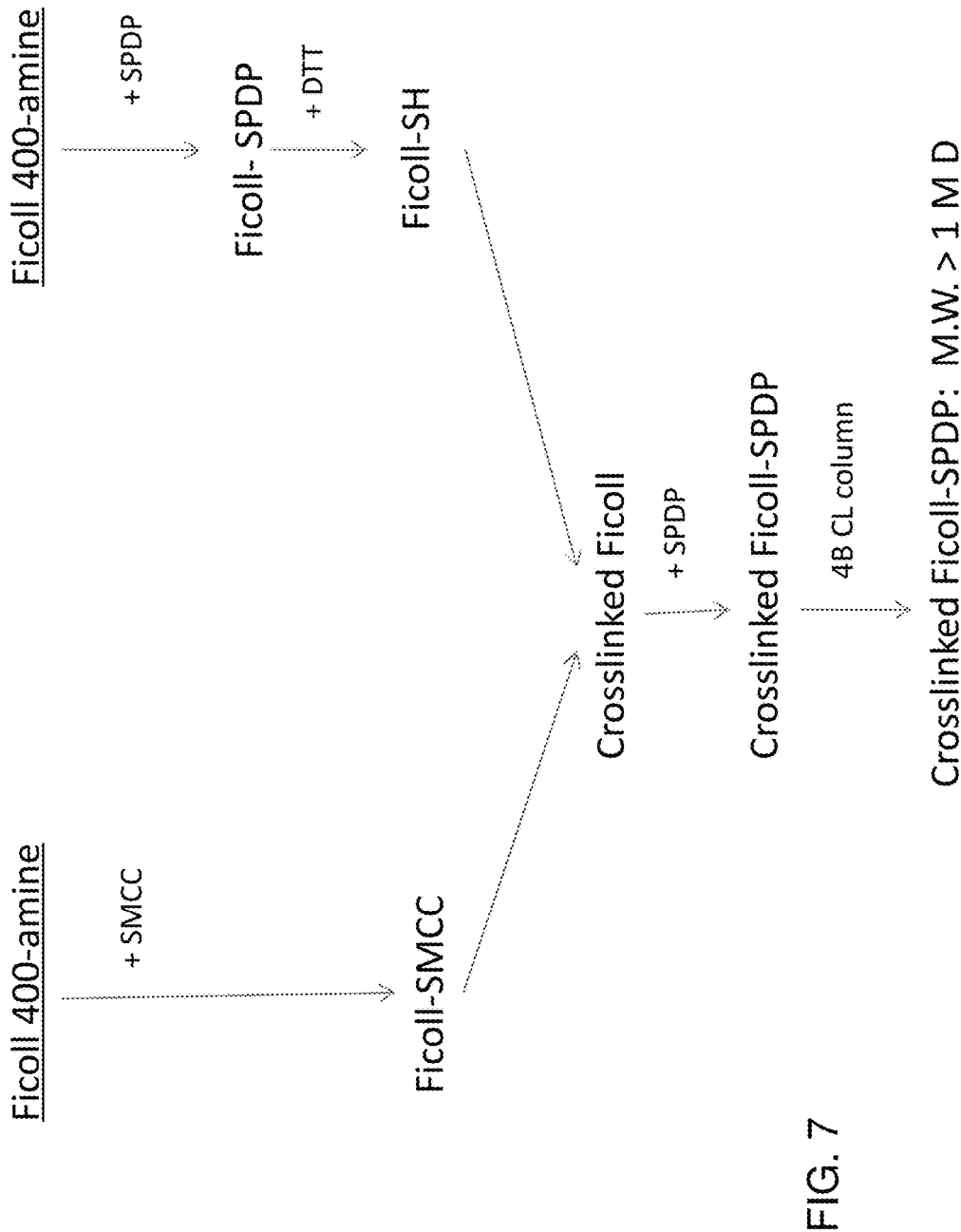
FIG. 7 shows a flow chart of the preparation crosslinked FICOLL® 400-SPDP.

Crosslinked FICOLL® 400-SPDP (succinimydyl 6-[3-[2-pyridyldithio]-proprionamido]hexanoate, Invitrogen) was prepared according to Example 1 of US 2011/0312105, which is incorporated herein by reference. FIG. 7 shows a flow chart of its preparation.

Example 4. Preparation of Cy5-Streptavidin

32 µL of Cy 5-NHS (GE Healthcare) at 5 mg/ml in DMF reacted with 1 ml of streptavidin (Scripps Labs) at 2.4 mg/ml in 0.1 M sodium carbonate buffer pH 9.5 for 40 minutes at 30° C. Applying the mixture to a PD 10 column (Pharmacia) removed unconjugated Cy 5. Spectral analysis indicated 2.8 Cy 5 linked per streptavidin molecule.

Example 4a. Preparation of Cy5-Antibody

Cy5-antibody is prepared according to Example 4 by replacing streptavidin with an antibody.

Example 5. Preparation of Cy5-StreptavidinCrosslinked FICOLL®

5.8 µL of SMCC (succinimidyl 4[N-malemidomethyl] cyclohexan-1-carboxylate, Pierce Chemical) at 10 mg/ml in DMF reacted with 2 mg Cy5-streptavidin (Example 4) in 1 ml PBS pH 7.4 for 1 hour at room temperature. Applying the mixture to a PD 10 column removed unbound SMCC.

The thiols on crosslinked FICOLL® 400-SPDP were deprotected by adding 30 µL DTT at 38 mg/ml to 1 mg crosslinked FICOLL® 400-SPDP in 1 ml PBS and reacting for 1 hour at room temperature followed by a PD 10 column to purify the crosslinked FICOLL®.

The Cy5-streptavidin-SMCC was mixed with crosslinked FICOLL® 400-SH and reacted overnight at room temperature. 10 µL NEM (Aldrich) at 12.5 mg/ml was then added and reacted for ½ hour at room temperature. The conjugate was then purified on a Sepharose 4B CL column. It was estimated that the conjugate carried about 20 to 30 streptavidins per FICOLL® (2 million Daltons), and 2-3 Cy5s per streptavidin.

Example 5a. Preparation of Cy5-Streptavidin-Crosslinked FICOLL®

Cy5-antibody-crosslinked FICOLL® is prepared according to Example 5 by replacing streptavidin with an antibody.

Example 6: Wide Range Protocol for BNP

For the first sequence of the wide range assay, BNP calibrators (Hytest) were spiked into normal, pooled human plasma then diluted 1 to 3 in PBS with 5 mg/ml BSA and 0.05% Tween 20 (assay buffer). The probe tip was immersed in the BNP sample wells and incubated for 1 minute at room temperature with the sample wells subjected to orbital movement (1 mm diameter stroke) at 50 rpm. The probe was held stationary. The probe was washed 3 times for 10 seconds in PBS, 0.05% Tween 20. After the wash sequence, the probe was immersed in a reagent solution containing biotinylated anti-BNP at 10 µg/ml in assay buffer, followed with 0.5 min incubation at 500 rpm, then a 3× wash sequence. Probes were then transferred to an amplification solution Cy5-streptavidin-Cx FICOLL®. After 0.5 minute incubation at 500 rpm, the probes were taken through a wash sequence. Fluorescence at the distal tip of the probe was then measured and results shown in Table 1 under 1st Read.

The second sequence consisted of transferring the probe back to the same sample wells and performed the assay with the cyclic amplification procedure. The probe was incubated for 5 min. at 750 rpm in the sample, followed by a wash sequence. Three cycles were then performed, where for each cycle the probe was immersed in the same biotinylated anti-BNP solution for 2 min at 500 rpm, followed by a wash sequence, immersed in the same Cy5-streptavidin-Cx FICOLL® solution for 1 minute at 500 rpm, followed by a wash sequence. After the first cycle (Amp1) and the third cycle (Amp3), the fluorescence on the probe tip was measured. The data are shown on Table 1. Each data point is a mean of duplicates. "Sat" refers to saturated signal.

TABLE 1

| [BNP] | | 2$^{nd}$ Read | |
|---|---|---|---|
| (ng/ml) | 1$^{st}$ Read | Amp 1 | Amp 3 |
| 50 | 5.2 | 12.6 | Sat |
| 25 | 3.5 | 10.2 | Sat |
| 12 | 2.1 | 7.3 | Sat |
| 6 | 1.4 | 6.6 | Sat |
| 3 | 0.7 | 3.7 | 14.3 |
| 1 | 0.27 | 1.85 | 8.43 |
| 0.3 | 0.1 | 0.83 | 3.93 |
| 0.1 | 0.004 | 0.3 | 1.13 |
| 0.05 | 0.01 | | 0.43 |
| 0.012 | 0.01 | | 0.28 |
| 0 | 0.01 | 0 | 0.09 |

The results of Table 1 show that the quantification range for the first sequence (1st Read) is from about 1-50 ng/ml, for the second sequence with one amplification cycle (Amp 1) is from 0.3-25 ng/ml, and for the second sequence with three amplification cycles (Amp 3) is from 0.012-3 ng/ml. The combination of the results of the first sequence and the second sequence yield a much greater overall range (0.01-50 ng/mL, 5000 fold) than relying on a single sequence.

Example 7: Wide Range Protocol for NT-proBNP

NT-proBNP calibrators were obtained from Hytest, Finland. The Assays were performed similarly to that of Example 6, except two amplification cycles (Amp 2) were carried out in the second sequence.

The data are shown on Table 2.

TABLE 2

| NTProBNP ng/ml | 1$^{st}$ Read | 2$^{nd}$ Read Amp 2 |
|---|---|---|
| 135 | 7.25 | 20 |
| 45.3 | 4.66 | 20 |
| 15.1 | 2.01 | 20 |
| 5.04 | 0.81 | 16.4 |
| 1.67 | 0.23 | 9.29 |
| 0.56 | 0.12 | 5.25 |
| 0.18 | 0.07 | 2.25 |
| 0.06 | 0.05 | 0.94 |
| 0 | 0.06 | 0.13 |

The results of Table 2 show that the quantification range for the first sequence (1st Read) is from about 0.56-135 ng/ml, for the second sequence with two amplification cycles (Amp 2) is from 0.06-5.04 ng/ml. The combination of the results of the first sequence and the second sequence yield a much greater overall range (0.06-135 ng/mL, 2250 fold) than relying on a single sequence.

As a comparison with an industry standard, Roche Cobas NTproBNP assay range is 0.06-35 ng/mL (583 fold). Roche's quantification range is about 4-fold lower than that of the present invention.

Example 8: Wide Range Protocol for PCT

PCT calibrators were obtained from Hytest, Finland. The Assays were performed similarly to that of Example 5, except two amplification cycles (Amp 2) were carried out in the second sequence.

The data are shown on Table 3.

TABLE 3

| [PCT], ng/ml ng/ml | 1$^{st}$ Read | 2$^{nd}$ Read Amp 2 |
|---|---|---|
| 400 | 5.84 | 20 |
| 133 | 2.11 | 20 |
| 44 | 0.81 | 20 |
| 14.8 | 0.28 | 20 |
| 4.9 | 0.11 | 11.82 |
| 1.64 | 0.07 | 4.54 |
| 0.54 | 0.04 | 1.68 |
| 0.18 | 0.04 | 0.83 |
| 0.06 | 0.04 | 0.54 |
| 0 | 0.04 | 0.38 |

The results of Table 3 show that the quantification range for the first sequence (1st Read) is from about 4.9-400 ng/ml, for the second sequence with two amplification cycles (Amp 2) is from 0.06-14.8 ng/ml. The combination of the results of the first sequence and the second sequence yield a much greater overall range (0.06-400 ng/mL, 6667 fold) than relying on a single sequence.

As a comparison with an industry standard, Roche Cobas PCT assay range is 0.06-100 ng/mL (1667 fold). Roche's quantification range is about 4-fold lower than that of the present invention.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims.

What is claimed is:

1. A method of detecting an analyte in a wide concentration range in a liquid sample, comprising the steps in the order of:
    (a) obtaining a probe having a first antibody immobilized on the tip of the probe, wherein the diameter of the tip surface area is ≤5 mm;
    (b) dipping the probe tip into a sample vessel containing a sample solution having an analyte to bind the analyte to the first antibody on the probe tip;
    (c) dipping the probe tip into a reagent vessel containing a reagent solution comprising a reagent of a second antibody conjugated with a first member of a binding pair to bind the reagent to the analyte, wherein the first antibody and the second antibody are antibodies against the analyte;
    (d) dipping the probe tip into a washing vessel containing a wash solution to wash the probe tip;
    (e) dipping the probe tip into an amplification vessel containing an amplification solution comprising a second member of the binding pair conjugated with one or more luminescent labels, to form an immunocomplex of the analyte, the first antibody, the second antibody, and the first and the second members of the binding pair on the probe tip;

(f) obtaining a first result by measuring a luminescent signal of the immunocomplex formed on the probe tip;

(g) dipping the probe tip of (f) into the same sample vessel and flowing the sample solution laterally in the sample vessel in a more favorable binding condition of a longer reaction time and/or more agitation than step (b), to bind additional analyte in the sample to the first antibody on the probe tip;

(h) repeating steps (c) to (e) 1-10 times to obtain a final immunocomplex; and (i) obtaining a second result by measuring a luminescent signal of the final immunocomplex formed on the probe tip; and (j) combining the first and the second results and analyzing the analyte concentration;

whereby the analyte is quantitated over the wide concentration range.

2. The method according to claim 1, wherein said amplification solution comprises a polymer conjugated with at least 5 molecules of the second member of the binding pair and at least 25 molecules of the one or more luminescent labels, wherein the polymer has a molecular weight of at least 1 million Daltons.

3. The method according to claim 1, wherein the diameter of the tip surface area is ≤about 2 mm.

4. The method according to claim 1, wherein the binding pair is a hapten and its antibody, a ligand and its receptor, complementary strands of nucleic acids, or lectin and carbohydrates.

5. The method according to claim 4, wherein the binding pair is biotin and streptavidin, biotin and avidin, biotin and streptavidin, biotin and neutravidin, fluorescein and anti-fluorescein, digioxigenin and anti-digioxigenin, or DNP and anti-DNP.

6. The method according to claim 5, wherein the first member of the binding pair is biotin and the second member of the binding pair is streptavidin.

7. The method according to claim 1, wherein the polymer is a polysaccharide, a polynucleotide, a dendrimer, a polyols, or polyethylene glycol.

8. The method according to claim 1, wherein the polymer is a branched polysaccharide.

9. The method according to claim 1, wherein the step (h) repeats steps (c) to (e) 1-3 times.

10. The method according to claim 1, wherein the luminescent label is a fluorescent dye selected from the group consisting of: cyanine, coumarin, xanthene and a derivative thereof.

11. The method according to claim 1, wherein the luminescent label is a chemiluminescent label of ruthenium(II) tris-bipyridine or luminol.

12. The method according to claim 1, wherein the analyte is basic natriuretic peptide, the N-terminal prohormone of brain natriuretic peptide, or procalcitonin.

* * * * *